United States Patent [19]
Behler et al.

[11] Patent Number: 4,936,551
[45] Date of Patent: Jun. 26, 1990

[54] FATTY ACID POLYOXYALKYL ESTER SULFONATES, A PROCESS FOR THEIR PRODUCTION AND THEIR USE AS SURFACTANTS

[75] Inventors: Ansgar Behler, Bottrop; Robert Piorr, Ratingen-Hoesel; Michael Schaefer, Erkrath, all of Fed. Rep. of Germany

[73] Assignee: Henkel Kommanditgesellschaft auf Aktien, Duesseldorf-Holthausen, Fed. Rep. of Germany

[21] Appl. No.: 207,609

[22] Filed: Jun. 15, 1988

[30] Foreign Application Priority Data

Jun. 15, 1987 [DE] Fed. Rep. of Germany ....... 3720000

[51] Int. Cl.$^5$ ............................................. C07C 143/02
[52] U.S. Cl. ..................................... 260/400; 252/555
[58] Field of Search .......................... 260/400; 252/555

[56] References Cited

U.S. PATENT DOCUMENTS

| | | | |
|---|---|---|---|
| 1,985,747 | 12/1934 | Steindorff et al. | 260/151 |
| 3,268,563 | 8/1966 | Shen et al. | 260/400 |
| 4,792,419 | 12/1988 | Piorr et al. | 260/513 |

FOREIGN PATENT DOCUMENTS

| | | | |
|---|---|---|---|
| 464871 | 5/1950 | Canada | 260/400 |
| 3331513 | 3/1985 | Fed. Rep. of Germany . | |
| 3612481 | 10/1987 | Fed. Rep. of Germany | 260/400 |
| 585219 | 2/1947 | United Kingdom . | |
| 848224 | 9/1960 | United Kingdom . | |
| 848225 | 9/1960 | United Kingdom . | |
| 1050534 | 12/1966 | United Kingdom | 260/400 |

*Primary Examiner*—Bruce Gray
*Attorney, Agent, or Firm*—Ernest G. Szoke; Wayne C. Jaeschke; Real J. Grandmaison

[57] ABSTRACT

Fatty acid polyoxyalkyl ester sulfonates obtained by reaction of $C_{11}$–$C_{22}$ monounsaturated monocarboxylic acid polyoxyalkyl esters corresponding to the following general formula $$C_mH_{2m-1}-CO-(O-C_nH_{2n})_x-OR \qquad (I)$$

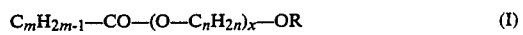

in which
R is a $C_1$–$C_{22}$ alkyl radical or a $C_3$–$C_{22}$ alkenyl radical,
m has a value of 10, 15, 17, 19 or 21,
n has a value of 2 or 3 and
x has a value of 1 to 20, with sulfur trioxide and subsequent reaction of the sulfonated fatty acid polyoxyalkyl ester obtained with aqueous alkali metal salts. The sulfonates have high surface activity and favorable performance properties as surfactants.

10 Claims, No Drawings

FATTY ACID POLYOXYALKYL ESTER SULFONATES, A PROCESS FOR THEIR PRODUCTION AND THEIR USE AS SURFACTANTS

BACKGROUND OF THE INVENTION

1. Field of the Invention

This invention relates to fatty acid polyoxyalkyl ester sulfonates obtained by reaction of $C_{11}$–$C_{22}$ monounsaturated monocarboxylic acid polyoxyalkyl esters with sulfur trioxide and subsequent reaction of the sulfonated fatty acid polyoxyalkyl ester obtained with aqueous alkali metal salts.

2. Discussion of Related Art

Commercially the most important anionic surfactants are those which contain a sulfone group as a water-solubilizing group. Such surfactants may be divided into sulfate surfactants and sulfonate surfactants.

Sulfate surfactants are semiester salts of sulfuric acid. The most important representatives of this subgroup are the alkyl ether sulfates which, by virtue of their glycol ether groups, are readily soluble in water and are therefore particularly suitable for use in the production of liquid detergents and cleaning preparations. One disadvantage of these compounds, however, is their poor hydrolysis stability so that they cannot be used for acidic cleaning preparations.

Sulfonate surfactants include the salts of alkylsulfonic acids which are stable to hydrolysis, even in acidic medium. Sulfonate surfactants which contain glycol ether groups to improve their solubility in water include the alkyl glycol ether sulfonates known from U.S. Pat. 1,985,747, the alkyl glyceryl ether sulfonates known from German Patents 1,075,779 and 1,081,172 and the fatty alkyl (polyoxyalkyl) lower alkyl ether sulfonates known from German Patent 33 31 513.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that fatty acid polyoxyalkyl ester sulfonates obtained by sulfonation of monocarboxylic acid polyoxyalkyl esters corresponding to general formula I below may be produced from readily obtainable starting materials. Surprisingly, the ester functions remain largely intact during the sulfonation and hydrolysis steps.

More particularly, the fatty acid polyoxyalkyl ester sulfonates of this invention are provided by reaction of $C_{11}$–$C_{22}$ monounsaturated monocarboxylic acid polyoxyalkyl esters corresponding to the following general formula $$C_mH_{2m-1}-CO-(O-C_nH_{2n})_x-OR \qquad (I)$$

in which

R is a $C_1$–$C_{22}$ alkyl radical or a $C_3$–$C_{22}$ alkenyl radical, m has a value of 10, 15, 17, 19 or 21, n has a value of 2 or 3 and x has a value of 1 to 20, with sulfur trioxide and subsequent reaction of the sulfonated fatty acid polyoxyalkyl ester obtained with an aqueous alkali metal salt.

Preference is attributed to fatty acid polyoxyalkyl ester sulfonates according to the invention in which the fatty acid residue corresponding to the following formula

$$C_mH_{2m-1}-CO-$$

is a residue derived from oleic acid (m=17). Alternatively, the fatty acid residue may be derived from erucic acid (m=21) or from undecylenic acid (m=10).

Fatty acid mixtures rich in oleic acid or erucic acid, of the type obtainable from animal fats, marine-animal and/or vegetable origin, rather than pure oleic acid or erucic acid, are preferably used for the production of the starting compounds corresponding to formula (I).

Typical fatty acid mixtures rich in oleic acid or, alternatively, erucic acid suitable for this purpose have the compositions shown in Table 1 below.

TABLE 1

| | Composition of typical fatty acids (in % by weight) | | | |
|---|---|---|---|---|
| | Origin | | | |
| Fatty acid | Beef tallow | Sunflower I | Sunflower II[1] | Rape |
| $C_{12}$ | 1.0 | — | — | — |
| $C_{14}$ | 3.0 | — | — | 0.5 |
| $C_{15}$ | 0.5 | — | — | — |
| $C_{16}$ | 5.0 | 6.0 | 3.5 | 2 |
| $C_{16}:1$* | 6.0 | — | — | — |
| $C_{17}$ | 1.0 | — | — | — |
| $C_{18}$ | 2.0 | 4.0 | 3.5 | 1 |
| $C_{18}:1$* | 70.0 | 28 | 85 | 15 |
| $C_{18}:2$* | 10.0 | 61 | 7 | 15 |
| $C_{18}:3$* | 0.5 | — | — | 7 |
| $C_{20}$ | — | 0.5 | 1 | 0.5 |
| $C_{20}:1$* | 1.0 | — | — | 7 |
| $C_{22}$ | — | — | — | 50 |

[1]Sunflower oil according to U.S. Pat. No. 4,627,192
*The number after the colon indicates how many carbon-carbon double bonds are present.

Undecylenic (10) is industrially obtained in relatively pure form from ricinoleic acid.

In another preferred embodiment of the invention, the R group is an aliphatic $C_1$–$C_{22}$ alkyl group. Particularly preferred R groups include those formed by the residue of a saturated or monounsaturated $C_{12}$–$C_{22}$ fatty alcohol. Where the R group is a monounsaturated alcohol, more especially a $C_{12}$–$C_{22}$ fatty alcohol, the starting compounds of general formula I contain an olefinic double bond in the acid portion and another olefinic double bond in the alcohol portion. In such cases, it is possible to introduce two sulfonate groups per monocarboxylic acid polyoxyalkyl ester molecule.

Fatty alcohols obtained by hydrogenation of technical grade fatty acid mixtures obtained from animal fats, marine-animal and/or vegetable origin, or alkyl esters thereof are preferably used for the production of the starting compounds of formula I.

Before the reaction with the monocarboxylic acids, the $C_1$–$C_{22}$ alcohols mentioned above are polyalkoxylated in the usual way with ethylene oxide and/or propylene oxide. Each alcohol molecule may be reacted with 1 to 20, and preferably with 2 to 12, moles of alkylene oxides. In the reaction with ethylene oxide and propylene oxide, the products may have a blockform or random distribution of the propylene oxide groups.

The present invention also relates to a process for the production of fatty acid polyoxyalkyl ester sulfonates

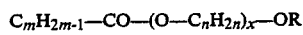

by reaction of monounsaturated $C_{11}$–$C_{22}$ monocarboxylic acid polyoxyalkyl esters corresponding to general formula I, in which R, m, n and x are as defined above, with sulfur trioxide and subsequent reaction of the sulfonated fatty acid polyoxyalkyl ester obtained with aqueous alkali metal salts. Finally, the invention relates to the process of using the fatty acid polyoxyalkyl ester sulfonates described above as surfactants.

The structure of the fatty acid polyoxyalkyl ester sulfonates according to the invention has not yet been definitively determined. By analogy with sulfonated olefins, however, the following alkene and hydroxyalkane structures I and II and Ia and IIa may be postulated:

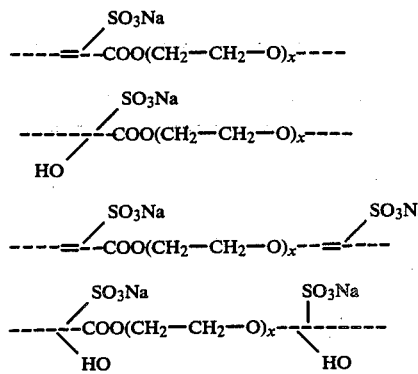

The sulfonation of the $C_{11}$–$C_{22}$ monounsaturated monocarboxylic acid polyoxyalkyl esters corresponding to general formula I is preferably carried out with gaseous sulfur trioxide at a temperature of from 20° to 100° C. This reaction may be carried out continuously in standard reactors suitable for the sulfonation of fatty alcohols, fatty acid esters, alkyl benzene or olefins, more especially of the falling film type. The sulfur trioxide is contacted with the monocarboxylic acid polyoxyalkyl esters of general formula I in air- or nitrogen-diluted form, preferably in the form of a gas mixture containing about 1–10% by volume of sulfur trioxide, advantageously at a temperature of 5° to 40° C.

The crude sulfonation product is then introduced into an aqueous solution of an alkali metal hydroxide, more especially sodium hydroxide, or other bases, for example amines, which should be present in a quantity of 1 to 1.2 moles base per mole added sulfur trioxide. The slight excess of base serves to neutralize the gaseous sulfur trioxide dissolved in the sulfonation product. Sodium hydroxide is preferably used as the alkali metal hydroxide, although potassium hydroxide may also be used. The concentration of the alkali metal hydroxide solution is selected so that the end product forms a low-viscosity solution.

Besides the desired sulfonates, the reaction product also contains sultones. The formation of sultones is a secondary reaction product known per se in the sulfonation of olefinic double bonds which also occurs in the process according to the invention. To convert the undesired sultones in the reaction product into hydroxysulfonates or unsaturated sulfonates, the aqueous solution has to be subjected to hydrolysis.

The hydrolysis is carried out by heating the solution at a pH value kept at 7 by the controlled addition of alkali metal hydroxide until the sultones have been completely destroyed. The time needed for this purpose depends on the hydrolysis conditions. Destruction of the sultones can be achieved in 4 to 6 hours, for example, at boiling temperature under normal pressure and very much more quickly under pressure at higher temperatures, the end of the hydrolysis reaction being reflected in the fact that the pH value of the reaction mixture remains constant in the absence of any further addition of alkali metal hydroxide.

In the process according to the invention, the fatty acid polyoxyalkyl ester sulfonates accumulate in the form of dark-yellow to light-yellow aqueous alkaline solutions. If desired, they may be bleached in known manner with hydrogen peroxide solution or sodium hypochlorite.

For stabilization against bacterial infestation, the solutions are best preserved with preservatives known from the prior art, for example p-hydroxybenzoate, sorbic acid and the like.

The starting compounds of general formula I may be obtained by methods known from the literature. They are produced from aliphatic saturated $C_1$–$C_{22}$ alcohols based on natural or synthetic alcohols or monounsaturated $C_3$–$C_{22}$ alcohols, for example methanol, ethanol, propanol, butanol, hexanol, octanol, decanol; and from oleyl alcohol or technical grade alcohol cuts consisting predominantly of oleyl alcohol, palmitoleyl alcohol and linoleyl alcohol. Small proportions of saturated alcohols, for example cetyl and stearyl alcohol, are not harmful, particularly if the products obtained from the alcohols by alkoxylation are soluble in water. Other suitable unsaturated alcohols may be obtained by hydrogenation of oleic acid or technical grade oleic acid and are commercially available. Cetyl-oleyl and oleyl-linoleyl alcohol cuts having iodine values of 70 to 130 are preferred.

The alkoxylation of alcohols with ethylene oxide and/or propylene oxide is a process which has long been carried out on an industrial scale. Mixtures of homologous alkoxylates are obtained, corresponding in their average degree of alkoxylation to the quantity of added alkylene oxide.

The polyalkoxylated alcohols obtained in this manner are then reacted with the $C_{11}$–$C_{22}$ monounsaturated monocarboxylic acids in the usual way, for example in the presence of esterification catalysts, such as tin powder.

The fatty acid polyoxyalkyl ester sulfonates according to the invention possess high surface activity and favorable performance properties as surfactants. Their wetting power with respect to fabrics is particularly favorable. By virtue of their high solubility in water and their satisfactory emulsifying power, the products are suitable for use both as industrial wetting agents and in detergents and cleaning preparations. Particular emphasis is also placed on their extremely light color, even without bleaching, and their stability against hydrolysis in alkaline media.

The invention is further illustrated by the following Example.

EXAMPLE

Oleic acid decaglycol ethyl ester sodium sulfonate preparation

In a standing laboratory reactor, 363.3 g (0.5 mole) of oleic acid decaglycol ethyl ester were heated to 30° C. 40 g of sulfur trioxide (0.5 mole; produced by evaporation of 65% oleum) diluted with nitrogen (5% by volume $SO_3$ in a stream of nitrogen) were introduced over a period of 50 minutes. Following a further 30-minute period, the acidic sulfonation product was introduced into water together with an aqueous 25% sodium hydroxide solution. After heating to 90° C., NaOH was added until a constant pH value of 7 was established. This required a total of 0.51 mole NaOH. The reaction product obtained was clearly soluble in water (30%).

The chemical-physical characteristic data of the compound thus obtained are shown in Table 2 together with those of other compounds similarly prepared in accordance with the Example.

Table 3 shows the saponification values (SV) of some of the compounds produced in the form of the actual SV, the desired SV and the actual SV/desired SV quotient.

Table 3 clearly shows that the ester bond remained largely intact during the sulfonation and the subsequent neutralization and hydrolysis steps.

TABLE 2

$C_{17}H_{33}$—CO—$(CH_2CH_2O)_x$—OR.$SO_3Na$

| Compound no. | x | R | WAS (%)[1] | $Na_2SO_4$ (% by wt.) | Color value[2] | Active substance[4] (O) |
|---|---|---|---|---|---|---|
| 1 | 10 | $C_2H_5$ | 23.7 | 0.6 | 29 | 35.1 |
| 2 | 2.9 | $C_{10}H_{21}$ | 19.8 | 0.7 | 45 | 25.3 |
| 3 | 7 | $C_{12}$-$C_{14}$ | 28.9 | 0.4 | | 29.6 |
| 4 | 3 | $C_2H_5$ | 23.0 | 1.7 | | 32.0 |
| 5 | 4 | $C_8H_{17}$ | 18.8 | 0.6 | | 25.0 |
| 6 | 5 | $C_{16}H_{18}$[3] | 25.8 | 1.4 | | |

[1]Washing-active substance (DGF method H-III-10)
[2]Klett color value (NaOCl bleach; 1 cm cell)
[3]Mixture of myristyl and oleyl alcohol
[4]Dry residue

TABLE 3

| Compound no. | Actual SV | Desired SV | Actual SV / Desired SV |
|---|---|---|---|
| 1 | 66.49 | 67.6 | 0.98 |
| 3 | 47.25 | 60.1 | 0.71 |
| 4 | 93.89 | 103.5 | 0.91 |

We claim:

1. Fatty acid polyoxyalkyl ester sulfonate obtained by reaction of a $C_{11}$-$C_{22}$ monounsaturated monocarboxylic acid polyalkyl ester corresponding to the following formula $$C_mH_{2m-1}-CO-(O-C_nH_{2n})_x-OR \quad (I)$$

in which
R is a $C_1$-$C_{22}$ alkyl radical or a $C_3$-$C_{22}$ alkenyl radical,
m has a value of 10, 15, 17, 19 or 21,
n has a value or 2 or 3 and
x has a value of 1 to 20, with sulfur trioxide and subsequent reaction of the sulfonated fatty acid polyoxyalkyl ester obtained with an aqueous alkali metal salt.

2. Fatty acid polyoxyalkyl ester sulfonate as in claim 1, wherein the fatty acid radical corresponding to the following formula $$C_mH_{2m-1}-CO-$$

is a radical derived from oleic acid.

3. Fatty acid polyoxyalkyl ester sulfonate as in claim 1 wherein the fatty acid radical corresponding to the following formula $$C_mH_{2m-1}-CO-$$

is a radical derived from erucic acid.

4. Fatty acid polyoxyalkyl ester sulfonate as in claim 1 wherein said $C_{11}$-$C_{22}$ monounsaturated monocarboxylic acid polyoxyalkyl ester is obtained from a fatty acid mixture rich in oleic acid or erucic acid obtained from animal fat, marine-animal or vegetable origin.

5. Fatty acid polyoxyalkyl ester sulfonate as in claim 1 wherein x has a value of about 2 to about 12.

6. Fatty acid polyoxyalkyl ester sulfonate as in claim 1 wherein the R group is an aliphatic $C_1$-$C_{22}$ alkyl group.

7. Fatty acid polyoxyalkyl ester sulfonate as in claim 1 wherein the R group is a radical of a saturated or monosaturated $C_{12}$-$C_{22}$ fatty alcohol.

8. Fatty acid polyoxyalkyl ester sulfonate as in claim 7 wherein said fatty alcohol is obtained by hydrogenation of a technical grade fatty acid mixture obtained from animal fat, marine-animal or vegetable origin, or alkyl esters thereof.

9. Fatty acid polyoxyalkyl ester sulfonate as in claim 1 wherein the fatty acid radical corresponding to the following formula $$C_mH_{2m-1}-CO-$$

is a radical derived from oleic acid, R is $C_2H_5$, and x has a value of 10.

10. A detergent composition containing a fatty acid polyoxyalkyl ester sulfonate obtained by reaction of $C_{11}$-$C_{22}$ monounsaturated monocarboxylic acid polyalkyl ester corresponding to the following formula $$C_mH_{2m-1}-CO-(O-C_nH_{2n})_x-OR \quad (I)$$

in which
R is a $C_1$-$C_{22}$ alkyl radical or a $C_3$-$C_{22}$ alkenyl radical,
m has a value of 10, 15, 17, 19 or 21,
n has a value of 2 or 3 and
x has a value of 1 to 20,
with sulfur trioxide and subsequent reaction of the sulfonated fatty acid polyoxyalkyl ester obtained with an aqueous alkali metal salt.

* * * * *